United States Patent [19]

Polansky

[11] Patent Number: 5,135,392
[45] Date of Patent: Aug. 4, 1992

[54] SELF CONTAINED DENTAL TRAY AND METHODS OF MAKING AND USE

[76] Inventor: Seymour Polansky, 72 Florence Rd., Riverside, Conn. 06878

[21] Appl. No.: 571,184

[22] Filed: Aug. 23, 1990

[51] Int. Cl.⁵ .......................... A61C 9/00; A61C 19/00
[52] U.S. Cl. .......................................... 433/37; 433/34; 433/48; 433/214
[58] Field of Search .................. 433/34, 36, 37, 47, 433/48, 213, 214; 264/16; 206/63.5, 83

[56] References Cited

U.S. PATENT DOCUMENTS

| | | | |
|---|---|---|---|
| 2,444,294 | 6/1948 | Jones | 206/83 |
| 2,963,786 | 12/1960 | Browning | 433/37 |
| 2,982,396 | 5/1961 | Shihadeh | 206/219 |
| 4,081,077 | 3/1978 | Franck | 206/83 |
| 4,167,618 | 9/1979 | Schmidt et al. | 528/424 |
| 4,368,040 | 1/1983 | Weissman | 433/36 |
| 4,672,081 | 6/1987 | Fisher et al. | 433/214 |
| 4,776,792 | 10/1988 | Wagner et al. | 433/71 |

FOREIGN PATENT DOCUMENTS 415596  7/1924  Fed. Rep. of Germany ...... 433/376

Primary Examiner—John J. Wilson
Assistant Examiner—Cindy A. Cherichetti

[57] ABSTRACT

A self contained dental tray for taking impressions of teeth and associated soft tissues which requires no previous application of adhesive to allow the teeth and impression to separate. In all of the embodiments the room temperature vulcanizable rubber and its hardener are included in the tray without the danger of premature hardening during shipping and storage.

15 Claims, 2 Drawing Sheets

SELF CONTAINED DENTAL TRAY AND METHODS OF MAKING AND USE

BACKGROUND OF THE INVENTION

The present invention relates to a self contained disposable dental tray for taking impressions of teeth and associated soft tissue, the materials therein, methods for its manufacture and the methods for using it to make impressions of teeth and associated soft tissue. At present, impressions of teeth and associated tissue are taken using room temperature vulcanized rubbers (RTVRs) that harden rapidly when mixed with hardener, generating temperatures which are not physiologically harmful to soft tissue. The materials and technology of taking dental impressions are disclosed in KIRK OTHMER' ENCYCLOPEDIA OF CHEMICAL TECHNOLOGY 3rd edition volume 20 pages 922 and 962 and are incorporated herein by reference. Further examples are disclosed in U.S. Pat. Nos. 3,453,242, 4,093,555; 4,167,618; 4,532,268; 4,009,687; 4,532,268 and are incorporated by reference herein.

In order to part the teeth from the impression, it is obviously mandatory that the impression adheres better to the tray than to the teeth. Currently to insure this, a layer of adhesive is placed at the bottom of the tray and then mixed RTVR and its Hardener are charged into the tray. A recent innovation, involves the application of self sticking dots of felt to replace the need for adhesive.

The RTVR's currently used are : polyimines from aziridino terminated polyethers, polysulfides, addition cured vinyl terminated polysiloxanols, and condensation cured polysiloxanols. These are supplied as a two part system, the hardened in one package and the RTVR in a second package. Modifiers and accelerators are also added. At present these two part systems are being sold as a single stroke double cylinder dispenser which simultaneously proportions and mixes the RTVR and hardener. The use of barrier layers between reactive materials to prevent premature mixing, when using a ome package system, is disclosed in U.S. Pat. No. 2,982,396 and is incorporated herein by reference.

SUMMARY OF THE INVENTION

There are two embodiments of this invention. The first is essentially a standard dental tray which requires no adhesive because of the mechanical design of the tray. There are mechanical means close to the bottom of the dental tray, —where they cannot interfere with the patient's teeth—which substitute for the adhesive presently used. These means are undercuts in the tray which makes separation of the RTVR impression from the teeth very difficult. This eliminates the need and expense of buying, storing and applying the adhesive and possibly even forgetting to apply the adhesive. A second embodiment of the invention in addition to eliminating the adhesive comprises means to package RTVR and Hardener in the correct proportions within the dental tray whereby they can be shipped, and stored with RTVR and hardener without premature hardening. Just before use, RTVR and hardener can be mixed in the dental tray thereby eliminating a mixing board. The tray is now truly totally self sufficient. It has the following advantages over the existing dental tray on the market. It requires no adhesive, thereby eliminating a possible source of error. It guarantees that the dentist uses the exact proportions of RTVR and hardener needed to produce a good impression. Storage space and inventory control is minimized. The barrier means may be attained in one of three ways.

1. A layer of RTVR and a layer of its Hardener are laid down on top of each other with a barrier layer between them. The barrier layer being compatible physically and chemically with the RTVR and Hardener and the curved RTVR.

2. the RTVR and hardener are laid down side by side rather than on top on top of each other. A solid removable barrier is placed between the layers of RTVR and hardener. The barrier material is non reactive with the RTVR and hardener and does not adhere to RTVR and hardener. After opening the package, the barrier layer is lifted upward and out of the tray which can then be used conventionally.

3. The correct amounts of RTVR and hardener are each packaged separately in squeezable tubes and are enclosed in the dental tray. The RTVR and hardener after being opened may be squeezed out directly in the tray and be mixed therein or alternatively may be squeezed onto a separate mixing board and mixed thereon and then transferred into the dental tray.

There is obviously a need for the advantages provided by this invention since the trade is constantly coming out with means for combining the RTVR and its hardener in one package and dental tray adhesive substitutes.

The trade has come out with single stroke double barreled plastic dispensers in order to package hardener and RTVR in one container without premature hardening. It is claimed that the extra initial cost of these systems is offset by the elimination of the waste accompanying the use of two part systems. There is no loss on mixing outside the dental tray since the mixing is done within it. The simple dental tray of this invention is obviously cheaper to fabricate than a single stroke double barreled part. The trade has also come out with adhesive spots which are presumably inexpensive and make the tray reusable. These are adhesive baked spots of felt. The adhesive face of the spots adhere to the tray and the RTVR adheres to the felt face thereby allowing the teeth to readily separate from the impression. The reusability issue is resolved by the fact that the disposible inexpensive self contained dental tray of this invention saves the cost:

1. of buying the adhesive,
2. washing and sterilizing the dental tray,
3. in time and labor to apply and remove the adhesive spots.

BRIEF DESCRIPTION OF THE DRAWINGS

In order that the invention be more readily understood, embodiments thereof represented in the drawings, will be described by way of purely illustrative and non restrictive examples, In these drawings.

Item (1) in each drawing represents the handle used by the technician or the dentist for manipulating the self contained dental tray in mixing, insertion in the patient's mouth, withdrawing it etc.

DESCRIPTION OF THE PREFERRED EMBODIMENTS

Figure 3A:
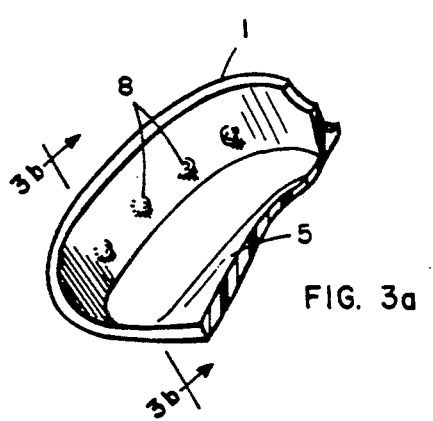
FIG. 3a. A view of the back showing a first embodiment having indentations for allowing the teeth and the impression to part without the need for an adhesive.
Figure 3B:
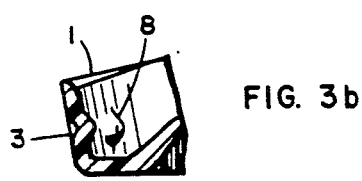
FIG. 3b. A side view showing the indentation at the periphery of the tray.
Figure 4A:
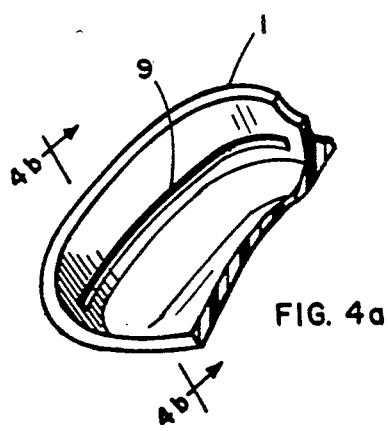
FIG. 4a. A second embodiment having a groove around the periphery to facilitate the parting of the impression from the teeth without recourse to an adhesive between the RTVR and its hardener.
Figure 4B:
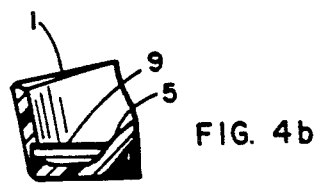
FIG. 4b. A side view showing the groove around the periphery of the tray.
Figure 5A:
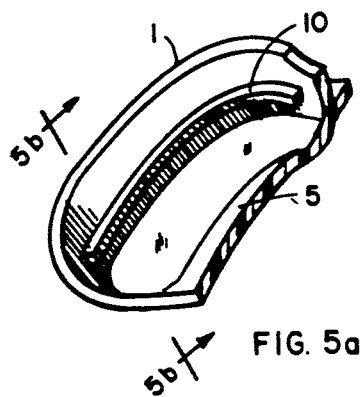
FIG. 5a. A third embodiment showing a ledge around the periphery of the tray to facilitate parting of teeth and impression.
Figure 5B:
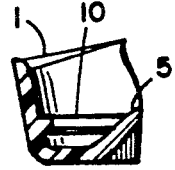
FIG. 5b. A side view of the above third embodiment.

The invention depends upon the fact that it is difficult if not impossible to part a molded object from a mold that has too many undercut details in it. There are several embodiments of this invention addressing this problem presented herein but is not limited to them. One uses a plurality of indentations close to the bottom of the tray (8) FIGS. 3a and 3b and which act similarly to the barbs on a fish hook. Another has a groove running about the periphery of the tray and may be at any height and is shown as 9 in FIGS. 4a and 4b. A third embodiment is a narrow ridge around the periphery of the tray close to the bottom, (10) of FIGS. 5a and 5b.

Figure 6:
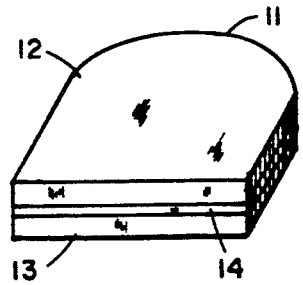
FIG. 6. An embodiment showing how the RTVR and its hardener are stored on top of each other without premature hardening of the RTVR by the use of a mixable and compatible barrier layer.

Another aspect of the invention is the use of the self contained dental tray for storage, shipping, and mixing of the RTVR and its Hardener in conjunction with the undercut feature described above. This can be achieved in any of three ways. The RTVR and Hardener (12 and 13) can be layered on top each other and separated by appropriate barrier materials (14) as is shown in FIG. 6. Low melting waxes, mineral oils, as well as silicone oils can be used for aziridino terminated polyethers and for polysulfide based systems. Vinyl terminated siloxanols are more sensitive but can be separated by vaseline like silicone formulations which are unreactive to siloxanol RTVRs.

Figure 1:
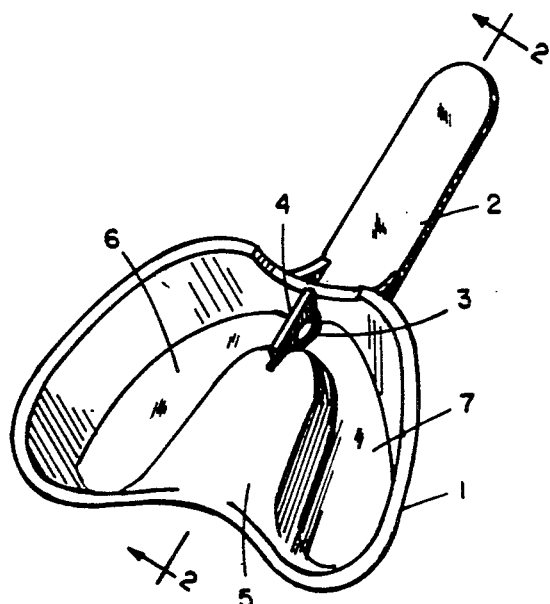
FIG. 1 is an isometric view of a self contained dental tray several embodiments of which can eliminate the need of an adhesive between the tray and the mixture of RTVR and hardener and embodiments which have means to prevent premature hardening of RTVR and its hardener. Various combinations of mechanical means as a tray adhesive and means to prevent premature hardening can be combined.
Figure 2:
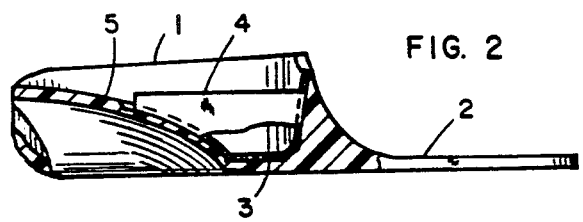
FIG. 2 is a side view through the center showing a slot in the center of the tray and a separator sitting therein whereby RTVR and its hardener can be kept apart during storage.

An alternative to the above, is to fill one side of the U-shaped self contained dental tray with the RTVR and the other side with its hardener. To keep them separated prior to mixing, a removable barrier (4) FIGS. 1 and 2 is inserted between them. The barrier is held in place by a slot (3) also shown in FIGS. 1 and 2. Prior to mixing the barrier is slid up and out of the slots and tray.

Figure 7:
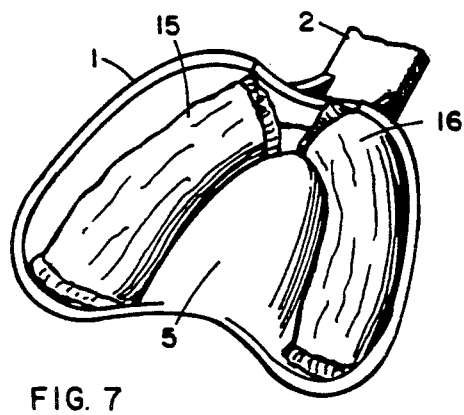
FIG. 7. An embodiment showing how the RTVR and its hardener are packed individually in sealed units, and which can be squeezed out just prior to use. The RTVR and its hardener may be mixed in the tray or on a external mixing board.

Another embodiment that allows the RTVR and its hardener to be stored within the tray prior to use is shown in FIG. 7 wherein (15) and (16) show the materials held in squeezable packages.

Figure 8:
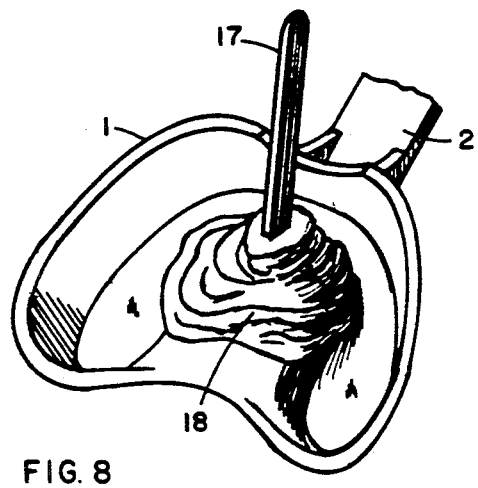
FIG. 8. Shows the RTVR and its hardener being mixed in the self contained dental tray.
Figure 9:
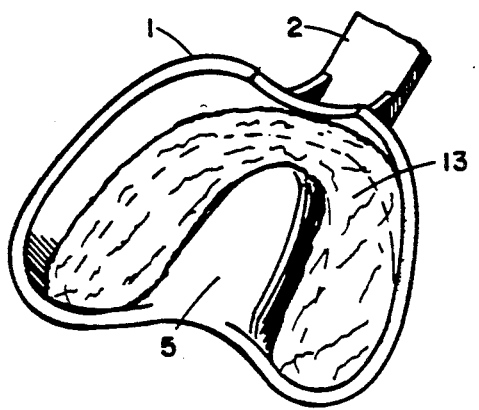
FIG. 9 shows the RTVR and hardener ready to be used in making a dental impression.
Figure 10:
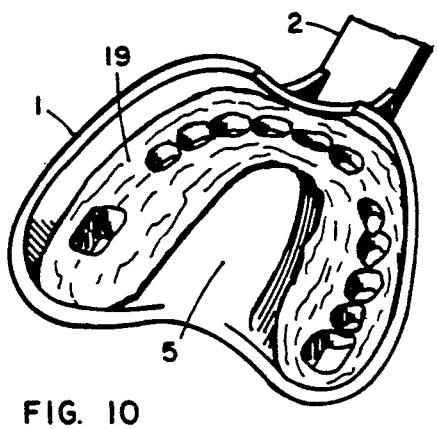
FIG. 10. A view showing a dental impression adhering to the tray after the patient has withdrawn his tenth from the tray.

FIG. 8 shows the RTVR and its hardener (18) being mixed by a disposable stirrer (17). In FIG. 9 we see the RTVR and Hardener just prior to having the patient clamp his teeth therein. FIG. 10 shows a typical dental impression including missing teeth (19). The tray and its contents are sealed by conventional sealing means, not shown, to prevent the loss of the RTVR and its hardener and the introduction of air or contaminents.

EXAMPLE 1

A cell was made by fusing two previously thermoformed plastic cells, one having a diameter of 23 mm's and the other 21 mm's. The top of the one with the smaller diameter had its top removed. This produced a tray having the equivalent to a groove around the periphery. The ingredients, an aziridino terminated, polyether, and the hardener supplied Impregum F), distributed by Premier Dental Products Co. of Norristown, Pa. were layered therein with a layer of was between them. After mixing the ingredients, a flat headed nail, head first, was inserted. After 20 minutes I tried to remove the nail from the hardened RTVR. To do this I had to tug back and forth as well as pull up very vigorously. This resulted in shattering the cell before I could remove the nail. A very well defined impression of the nail head was obtained nevertheless.

EXAMPLE 2

The above experiment was repeated using "Cinch" brand vinyl terminated Siloxanol room temperature vulcanized rubber supplied by the Parkell Corpn. of Long Island New York. No barrier layer was used in this experiment. The same results as in example 1 were obtained.

EXAMPLE 3

A test mold was made by thermoforming a cylindrical shape. Depressions were made into the cylinder wall a few mm's from the bottom, by pushing hot wires into the wall. The wires were removed when they were at room temperature leaving depressions very reminiscent of the bars on fish hooks. Examples 1 and 2 were repeated using these tests cells. The same results were obtained.

EXAMPLE 4

Test cells were made without any of the previously described undercut details of examples 1, 2, 3. As a substitute for these undercut details of adhesives. Tray Dot Adhesives supplied by Parkell were used. After the RTVRs were hardened and efforts were made to remove the nail head, the impression and the felt dots were removed from the tray and the nail head remained in the impression.

The results of these four examples prove that undercutting means are superior to the tray dot adhesives that are being supplied as an alternative to the liquid adhesives which they are supposed to replace.

EXAMPLE 5

Using the methods of example 3 make a series of indentations about the perimeter of a commercial dental tray. Fill with a well mixed amount of Impregum F and its catalyst. Have the patient bite into the tray and hold still for about 20 minutes. Have the patient withdraw from the impression. It will be seen that the impression remains with the tray.

EXAMPLE 6

Repeat example 5 using Cinch brand RTVR. The results should be the same.

EXAMPLE 7

Mold a dental tray based on the indented design of examples 5 and 6. Take impressions of teeth using Impragum in one case and Cinch in a second case. The results without the use of tray adhesive of tray dot adhesives should be the same.

EXAMPLE 8

Mold dental trays with a peripheral ridge close to the bottom of the tray and repeat the previous taking of impressions using Impragum in one case and Cinch in the second. The results should be the same.

EXAMPLE 9

Mold a slot commercial tray as shown in FIG. 2. Slide into the slots a tightly fitting plastic strip to serve as removable barrier to prevent the interaction of the RTVR And its hardener. Dress the bottom of the tray with a standard tray adhesive. Fill one of the created compartments with the RTVR and the other with hardener. In one example use Impragum, in a second example use Cinch. After a period of time, remove the barrier, mix and have a patient insert the teeth into the mixed material. Hold for a reasonable time, them remove the teeth. The results should be the same as in all the other examples.

EXAMPLE 10

Mold several dental trays, all having the slots and removable barriers described above, having the various undercut features described above. Note, do not use any kind of adhesive material. Repeat the procedures for taking dentalimpressions described above. The results should all be the same. Impressions having good definition and easy withdrawal of the tray with the impression should be achieved.

I claim:

1. A self contained dental tray for taking impressions of teeth and surrounding soft tissue containing a room temperature vulcanized rubber and its hardener which can be shipped and stored without premature hardening having mechanical means as a tray adhesive alternative to insure separation of the teeth from the impression, whereby the latter is held tightly to the tray safely and reproducibly comprising:
   a. a dental tray for taking impressions,
   b. said mechanical means as a tray adhesive alternative comprises undercut features in the wall of said tray which prevents said impression from being withdrawn easily from said tray,
   c. said room temperature vulcanized rubber, partially filling said tray,
   d. a barrier means between said room temperature vulcanized rubber and its hardener whereby they are prevented from reacting,
   e. said hardener or said room temperature vulcanized rubber filling the remainder of said tray, and
   f. an easily removed sealing means for said dental tray.

2. A self contained dental tray, as recited in claim 1 wherein:
   a. said room temperature vulcanized rubber, is in a first layer,
   b. said hardener for said vulcanized rubber, is in a second layer, and
   c. said means for preventing said first layer and said second layer from premature hardening is a mixable barrier layer between said layers which is compatable with the vulcanized rubber produced.

3. A self contained dental tray as recited in claim 2 wherein said mechanical means as a tray adhesive alternative comprises at least two indentation in the wall of said self contained dental tray.

4. A self contained dental tray as recited in claim 2 wherein said mechanical means as a tray adhesive alternative comprises a groove around the periphery of the tray.

5. A self contained dental tray as recited in claim 2 wherein said mechanical means as a tray adhesive alternative comprises a peripheral ridge close to the bottom of the tray.

6. A self contained dental tray, as recited in claim 1 wherein said room temperature vulcanized rubber, and said hardener are placed side by side and said means for preventing premature hardening of said room temperature vulcanized rubber is an easily removed piece of pastic placed, between said room temperature vulcanized rubber and said hardener, and which is held securely by a pair of slots in the wall of said tray.

7. A self contained dental tray as recited in claim 6 wherein said mechanical means as a tray adhesive alternative comprises at least two indentations in the wall of said self contained dental tray.

8. A self contained dental tray as recited in claim 6 wherein said mechanical means as a tray adhesive alternative comprises a groove around the periphery of the tray.

9. A self contained dental tray as recited in claim 6 wherein said mechanical means as a tray adhesive alternative comprises a peripheral ridge molded into the tray close to the bottom.

10. A method for producing a self contained dental tray comprising the steps of:
   a. Molding a dental tray having mechanical means (undercut features in the wall of said tray), as a dental tray adhesive alternative,
   b. partially filling said tray with a room temperature vulcanized rubber,
   c. placing a barrier means between a hardener for said room temperature vulcanized rubber and said room temperature vulcanized rubber,
   d. filling the remainder of said tray with said hardener for said room temperature vulcanized rubber in the proper proportion,
   e. sealing said tray.

11. A method for producing a self contained dental tray as recited in claim 10 wherein the step of making a barrier means comprises inserting between a layer of said hardener and a layer of said room temperature vulcanized rubber a layer of a mixable material which is compatable with the vulcanized room temperature vulcanized rubber.

12. A method for producing said self contained dental tray as recited in claim 10, wherein the step of making a barrier means comprises inserting a removable strip of plastic into slots at either end of the walls of said tray whereby said room temperature vulcanized rubber and its hardener on either side of said barrier are prevented from hardening prematurely.

13. A method for taking dental impressions using a self contained dental tray comprising the steps of:
   a. removing the seal from a self contained dental tray for taking impressions of teeth and surrounding soft tissue containing a room temperature vulcanized rubber and its hardener which can be shipped and stored without premature hardening, having a barrier means to prevent said hardening, and mechanical means (undercut features in the tray wall) as a tray adhesive alternative to insure separation of the teeth from the impression, whereby the latter is held tightly to the tray safely,
   b. mixing said room temperature vulcanized rubber and its Hardener making sure that the resulting mix is homogeneous,
   c. Having the patient bite into said mixture and holding for the time dictated by the vulcanizing cycle of said room temperature vulcanized rubber used,
   c. Disengaging the patient's teeth from the impression formed.

14. A method for taking dental impressions as recited in claim 1 wherein said barrier means is a mixable material that is compatable with the vulcanized product of said room temperature vulcanized rubber and said hardener, and wherein the step of mixing said room temperature vulcanized rubber and said hardener comprises mixing said room temperature vulcanized rubber and said hardener with said mixable barrier.

15. A method for taking dental impressions as recited in claim 13 wherein said barrier means comprises a strip of film between said room temperature vulcanized rubber and said hardener, and wherein the steps of mixing said room temperature vulcanized rubber and said hardener further comprises sliding said strip of film up and out of said tray.

* * * * *